United States Patent [19]

Linnau

[11] Patent Number: 5,094,949
[45] Date of Patent: Mar. 10, 1992

[54] USE OF CHYMOTRYPSIN FOR THE INACTIVATION OF PREKALLIKREIN ACTIVATOR

[75] Inventor: Yendra Linnau, Vienna, Austria

[73] Assignee: Immuno Aktiengesellschaft für chemisch-medizinische Produkte, Vienna, Austria

[21] Appl. No.: 315,163

[22] Filed: Feb. 24, 1989

[30] Foreign Application Priority Data

Feb. 26, 1988 [AT] Austria .................. A494/88

[51] Int. Cl.$^5$ .................. C12N 11/10; C07K 17/10; C07K 3/20; C07K 15/00
[52] U.S. Cl. .................. 435/174; 435/177; 435/178; 435/269; 424/85.8; 530/390.5; 530/831
[58] Field of Search ............ 424/101, 85.8; 435/269, 435/174–180, 68.1; 530/831, 389.7, 391, 380, 362, 363

[56] References Cited

U.S. PATENT DOCUMENTS

| | | |
|---|---|---|
| 4,251,510 | 2/1981 | Tankersley . |
| 4,272,521 | 6/1981 | Zuffi .................. 424/101 |
| 4,312,949 | 1/1982 | Ahrens .................. 435/269 |
| 4,608,253 | 8/1986 | Ohnishi et al. .................. 435/269 |
| 4,608,254 | 8/1986 | Philapitsch et al. . |
| 4,814,277 | 3/1989 | Eibl et al. .................. 435/269 |
| 4,886,758 | 12/1989 | Eibl et al. .................. 435/269 |

OTHER PUBLICATIONS

B. M. Alving et al., The New England Journal of Medicine, vol. 299, p. 66 (1978).

Primary Examiner—Jacqueline Stone
Attorney, Agent, or Firm—Burns, Doane, Swecker & Mathis

[57] ABSTRACT

In order to avoid the risk of undesired side reactions of blood products, the latter are produced from plasma by using chymotrypsin to inactivate prekallikrein activator. These preparations are obtained by the fractionated enrichment of plasma proteins, with the proviso that a chymotrypsin solution or immobilized chymotrypsin is added to the fractions at any stage of the fractionation process. Before completion of the preparations, the chymotrypsin or the immobilized trypsin is removed from the preparations.

3 Claims, No Drawings

USE OF CHYMOTRYPSIN FOR THE INACTIVATION OF PREKALLIKREIN ACTIVATOR

The invention relates to the production of blood products from human or animal plasma, in particular of albumin and immunoglobulin-G preparations, which preparations are obtained by the fractionated enrichment of plasma proteins.

Plasma contains Hageman factor (Factor XII), a proenzyme of prekallikrein activator (PKA). Activated Hageman factors (Factor XIIa and Factor XIIf) act upon the blood coagulation scheme, the fibrinolytic and the kallikrein-kinin systems.

These prekallikrein activators may be formed at the production of blood products from plasma, the preparations obtained, thus, having a PKA content. Blood products of this type, such as albumin and immunoglobulin-G preparations, if infused in relatively large amounts, may cause adverse side reactions, e.g., states of shock (cf. B. M. Alving et al., The New England Journal of Medicine, vol. 299 (1978), 66).

A method of inactivating incompatibility-reaction-causing substances in blood products, by using immobilized chymotrypsin is known from EP-A-0 120 835. However, in the first place, vasoactive side effects and anticomplementary activity were considered as incompatibiliaty reactions.

It is, furthermore, known to inactivate PKA. Thus, in U.S. Pat. No. 4,251,510 (Tankersley), the removal of PKA through adsorption by means of silica-containing substances is described. This involves the danger of getting traces of heavy metals getting into the preparations. Furthermore, the addition of inhibitors, such as $C_1$-esterase inhibitor, is recommended in U.S. Pat. No. 4,608,254 (Philapitsch et al.). Such inhibitors are hardly accessible.

The invention aims at avoiding such difficulties and has as its object to enable the preparation of blood products that avoid the risk of undesired side reactions and is based on the finding that chymotrypsin is apt to enzymatically cleave undesired prekallikrein activator and to render ineffective its capability of converting prekallikrein into kallikrein.

Accordingly, the invention consists in the use of chymotrypsin for the inactivation of prekallikrein activator at the production of blood products from human or animal plasma, in particular of albumin and immunoglobulin-G preparations, which preparations are obtained by the fractionated enrichment of plasma proteins, with the proviso that a chymotrypsin solution or immobilized chymotrypsin is added to the fractions at any stage of the fractionation process and the chymotrypsin or the immobilized chymotrypsin is removed from the preparations before completion of the same.

According to a preferred embodiment, the invention consists in the use of chymotrypsin at the production of albumin and immmunoglobulin-G preparations, with the proviso that chymotrypsin in the form of an aqueous solution is added to an aqueous solution of the enriched plasma proteins, the plasma proteins are precipitated by a protein precipitating agent and, thereby, are separated from the chymotrypsin solution, whereupon the plasma proteins are processed to finished preparations.

According to another preferred embodiment, the invention consists in the use of chymotrypsin at the production of albumin and immunoglobulin-G preparations, with the proviso that chymotrypsin immobilized at Sepharose is added to an aqueous solution of the enriched plasma proteins, the solid substances are then removed from the solution to separate the chymotrypsin and the solutions containing the proteins are processed to finished preparations.

The invention will be explained in more detail by way of the following examples:

EXAMPLE 1

Production of an albumin preparation

To 7 l of human blood plasma 8% ethyl alcohol is added at a pH of 7.2 and a temperature of −2° C., with a precipitate forming. After separation of the precipitate, the ethyl alcohol concentration is raised to 25% and the temperature is lowered to −6° C. The precipitate forming, which contains immunoglobulin, is separated, and the ethanol concentration of the supernatant is increased to 40% at a pH of 6.5 and a temperature of −7° C. The formed precipitate, which contains alpha- and beta-globulin, is separated and discarded.

The pH of the supernatant is adjusted to 5.4, with albumin precipitating. The latter is separated by centrifugation and is subjected to a further step of purification: the precipitate is dissolved in water and the ethanol concentration is adjusted to 10% at a pH of 4.8 and a temperature of −2° C.

The precipitate is separated and discarded; the ethyl alcohol concentration of the supernatant is raised to 40%, the temperature is lowered to −8° C. and the pH is adjusted to 5.1. The albumin precipitate is separated by centrifugation. To remove the ethanol, the dissolved precipitate is subjected to ultrafiltration and the albumin solution is sterile-filtered. The sterile albumin solution is incubated with 0.1 unit of chymotrypsin (Sigma, product number: C-4129, lot 85 F-8130) per 100 mg of albumin at +37° C. under stirring: after 48 hours the inactivation of PKA has been completed.

To remove the dissolved chymotrypsin, the albumin can be precipitated by means of 45% EtOH at −6° C. and separated from the supernatant containing the chymotrypsin. The albumin solution is then processed to an administrable preparation.

In the following, the effect of the addition of chymotrypsin according to the invention will be explained, wherein the technique and reagents indicated below are applied for determining the prekallikrein activator:

Technique: From a purified prekallikrein preparation (PKK), kallikrein (KK) is generated by means of a prekallikrein activator (PKA). The kallikrein amidolytically splits p-nitroanilide (pNA) from a specific chromogenic substrate. The concentration of pNA is measured photometrically at a wave length of 405 nm.

Reagents:

Buffer I: 6.06 g TRIS and 23.38 g NaCl are dissolved in about 500 ml $H_2O$ dist. and are adjusted to a pH of 8.0 with diluted HCl and filled up to 1000 ml with $H_2O$ dist.

Buffer II: 1.81 g TRIS, 1.02 g imidazole and 6.43 g NaCl are dissolved in about 500 ml $H_2O$ dist. and are adjusted to a pH of 7.9 with diluted HCl and filled up to 1000 ml with $H_2O$.

Chromogenic substrate:

S 2302 (Kabi) H-D-prolyl-L-phenylanyl-L-arginin-p-nitroanilid-dihydrochloride. A 10 m molar aqueous solution is prepared.

25 mg S 2302 in 4.1 ml H₂O dist.

Prekallikrein preparation: The production of the preparation is carried out acording to a prescription of Harpel modified by M. S. Horowitz (New York Blood Center). Human citrated plasma is treated with the help of DEAE cellulose. The fraction that has not been bound to DEAE cellulose contains the prekallikrein.

Positive control (standard): As standard (=reference value), an albumin preparation of the Bureau of Biologics (BoB) of the Food and Drug Administration, Bethesda, Md. 20205, U.S.A., is used. This preparation contains prekallikrein activator. The generation of kallikrein by this BoB standard constitutes the reference value 1 and is equated to 100%.

Sample: If necessary, the sample is used in the assay in a dissolved or dilute state.

Assay: In a water bath at a temperature of 37° C.
100 myl prekallikrein preparation
50 myl buffer I
25 myl sample
are pipetted into a plastic tube. After an incubation time of 15 min at 37° C.
300 myl buffer II
50 myl S 2302 substrate
are pipetted. This mixture is introduced into a photometer brought to a temperature of 37° C., and the increase in the optical density per minute Δ (OD/min) at a wave length of 405 nm is measured with a layer thickness of 10 mm.

The activity of a sample Δ (OD/min) is expressed factorially—relative to the OBRR standard by the number 1—or in % of the OBRR standard; 1% of the OBRR standard equals 1 International Unit.

In the instant Example 1, PKA inactivation proceeded as follows:

|  | PKA | Content of albumin (monomers) |
| --- | --- | --- |
| Beginning | 43 IU/ml | 87.6% |
| after 24 h | 4 IU/ml | 87.4% |
| after 48 h | 1 IU/ml | 87.0% |

EXAMPLE 2

Production of an albumin preparation

The preparation of the albumin solution was carried out as in Example 1; instead of the dissolved chymotrypsin, 0.25 ml of chymotrypsin immobilized on Sepharose was used per 100 mg of albumin. After termination of the PKA inactivation process, the water-insoluble chymotrypsin was removed by filtration and the albumin was processes to an administrable preparation.

The immobilized chymotrypsin was prepared in the following manner: 100 ml of Sepharose 4 B gel (Pharmacia), after washing with 400 ml distilled water, were mixed with 20 g bromocyan dissolved in 10 ml acetonitrile at a pH of 11.0. The reaction mixture was cooled by an ice bath. After removal of the liquid phase, the gel was mixed with 80 mg chymotrypsin (Sigma) dissolved in 100 ml 0.2 molar NaHCO₃. The non-bound trypsin is separated by filtration from the trypsin bound to the gel.

After mixture of the gel trypsin with 100 ml of a 1 molar glycine solution, it is thoroughly washed free of proteins with a 0.2 molar NaHCO₃ solution. Finally, the gel trypsin is suspended in 100 ml of a 0.9% NaCl solution—it is ready for use in PKA inactivation.

PKA inactivation proceeded as follows, the determination of the prekallikrein activator having been carried out as in Example 1.

|  | PKA | Content of albumin (monomers) |
| --- | --- | --- |
| Beginning | 35 IU/ml | 87.5% |
| after 24 h | 2 IU/ml | 86.3% |
| after 48 h | 1 IU/ml | 84.8% |

EXAMPLE 3

Production of an immunoglobulin-G preparation

Human blood plasma is mixed with 8% ethanol at a pH of 7.2 and a temperature of −2° C. After separation of the precipitate, the ethanol concentration is increased to 25%, the temperature simultaneously being lowered to −6° C. The precipitate, which contains immunoglobulin, is further purified by extraction with a phosphate-acetate buffer and is mixed with 12% ethanol at a pH of 5.3 and a temperature of −2° C.

The precipitate is discarded. The ethanol concentration of the supernatant is increased to 25% at a pH of 7.2 and a temperature of −10° C. The pasty immunoglobulin precipitated is collected and dissolved; the ethanol is removed by ultrafiltration.

For PKA inactivation, 1U of chymotrypsin (Sigma, product number C-4129) is added to the sterile solution per 100 mg immunoglobulin and is treated at +37° C. under stirring. After treatment, immunoglobulin was precipitated with 40% ethanol at −6° C. and thereby separated from chymotrypsin. Immunoglobulin was processed to an administrable preparation.

PKA inactivation proceeded as follows:

|  | PKA | Content of monomers IgG |
| --- | --- | --- |
| Beginning | 323 IU/ml | 88.5% |
| after 24 h | 4 IU/ml | 87.0% |
| after 48 h | 0 IU/ml | 84.6% |

EXAMPLE 4

Production of an immunoglobulin-G preparation

The production of the immunoglobulin-G-containing fraction was performed in the same manner as in Example 3.

Incubation was effected with immobilized chymotrypsin. 1.0 ml of immobilized chymotrypsin was added to 1,000 mg protein.

PKA inactivation proceeded as follows:

|  | PKA | Content of monomers IgG |
| --- | --- | --- |
| Beginning | 315 IU/ml | 88.6% |
| after 24 h | 22 IU/ml | 87.9% |
| after 48 h | 0 IU/ml | 85.8% |

What I claim is:

1. A method for the inactivation of prekallikrein activator during the production of immunoglobulin-G blood product preparations from human or animal plasma comprising the steps of (1) obtaining said preparations in a fractionation process by the enrichment in fractions of plasma proteins, (2) adding dissolved chymotrypsin or immobilized chymotrypsin to said fractions at any stage of said fractionation process and (3) removing the respective one of said dissolved chymotrypsin and immobilized chymotrypsin from said preparations before completion thereof.

2. A method for the inactivation of prekallikrein activator during the production of immunoglobulin-G blood product preparations from human or animal plasma comprising the steps of (1) obtaining said preparations in a fractionation process by the enrichment in fractions of plasma proteins, (2) adding an aqueous chymotrypsin solution to an aqueous solution of enriched plasma proteins at any stage of said fractionation process, (3) precipitating said plasma proteins by a protein precipitating agent so as to be separated from said chymotrypsin solution, and (4) processing said plasma proteins to finished preparations.

3. A method for the inactivation of prekallikrein activator during the production of immunoglobulin-G blood product preparations comprising the steps of (1) obtaining said preparations in a fractionation process by the enrichment in fractions of plasma proteins, (2) adding chymotrypsin immobilized on Sepharose to an aqueous solution of enriched plasma proteins at any stage of said fractionation process, (3) removing solid substances from said solution to separate said chymotrypsin and to obtain protein-containing solutions, and (4) processing said protein-containing solutions to finished preparations.

* * * * *